(12) United States Patent
Liu et al.

(10) Patent No.: US 10,950,796 B2
(45) Date of Patent: Mar. 16, 2021

(54) LIGHT-EMITTING ELEMENT AND DISPLAY DEVICE

(71) Applicant: Shanghai Tianma AM-OLED Co., Ltd., Shanghai (CN)

(72) Inventors: Ying Liu, Shanghai (CN); Xiangcheng Wang, Shanghai (CN); Jinghua Niu, Shanghai (CN); Peng Shu, Shanghai (CN)

(73) Assignee: SHANGHAI TIANMA AM-OLED CO., LTD., Shanghai (CN)

( * ) Notice: Subject to any disclaimer, the term of this patent is extended or adjusted under 35 U.S.C. 154(b) by 367 days.

(21) Appl. No.: 15/892,196

(22) Filed: Feb. 8, 2018

(65) Prior Publication Data

US 2019/0051834 A1 Feb. 14, 2019

(30) Foreign Application Priority Data

Aug. 14, 2017 (CN) .......................... 201710692601.7

(51) Int. Cl.
| | |
|---|---|
| H01L 51/00 | (2006.01) |
| C07D 213/22 | (2006.01) |
| C09K 11/06 | (2006.01) |
| C07C 211/61 | (2006.01) |
| C07D 251/24 | (2006.01) |
| C07C 13/72 | (2006.01) |
| H01L 51/50 | (2006.01) |

(52) U.S. Cl.
CPC .......... *H01L 51/0056* (2013.01); *C07C 13/72* (2013.01); *C07C 211/61* (2013.01); *C07D 213/22* (2013.01); *C07D 251/24* (2013.01); *C09K 11/06* (2013.01); *H01L 51/006* (2013.01); *H01L 51/0067* (2013.01); *H01L 51/5012* (2013.01); *C07C 2603/18* (2017.05); *C07C 2603/97* (2017.05); *C09K 2211/1018* (2013.01); *H01L 51/0058* (2013.01); *H01L 51/5004* (2013.01); *H01L 51/5056* (2013.01); *H01L 51/5076* (2013.01); *H01L 51/5088* (2013.01); *H01L 51/5092* (2013.01); *H01L 51/5096* (2013.01); *H01L 2251/552* (2013.01)

(58) Field of Classification Search
None
See application file for complete search history.

(56) References Cited

U.S. PATENT DOCUMENTS

| | | | | |
|---|---|---|---|---|
| 5,840,217 | A * | 11/1998 | Lupo | C07C 13/72 252/583 |
| 7,862,904 | B2 * | 1/2011 | Vestweber | C07C 13/567 257/103 |
| 8,859,111 | B2 * | 10/2014 | Parham | C07C 13/72 428/690 |
| 9,312,495 | B2 * | 4/2016 | Pflumm | C07C 211/61 |
| 2002/0034659 | A1 * | 3/2002 | Nishi | H01L 51/0094 428/690 |
| 2006/0049397 | A1 * | 3/2006 | Pfeiffer | C09K 11/06 257/40 |
| 2007/0116984 | A1 * | 5/2007 | Park | H01L 51/0074 428/690 |
| 2008/0303422 | A1 * | 12/2008 | Vestweber | C09K 11/06 313/504 |
| 2011/0227036 | A1 * | 9/2011 | Vaufrey | H01L 51/5016 257/13 |
| 2012/0228552 | A1 * | 9/2012 | Parham | H05B 33/14 252/301.16 |
| 2013/0009118 | A1 * | 1/2013 | Stoessel | H01L 51/0085 252/519.21 |
| 2014/0203216 | A1 * | 7/2014 | Parham | C09K 11/06 252/500 |

(Continued)

FOREIGN PATENT DOCUMENTS

| | | |
|---|---|---|
| CN | 1756824 A | 4/2006 |
| CN | 102077384 A | 5/2011 |

(Continued)

OTHER PUBLICATIONS

Liao et al. "A Novel Ambipolar Spirobifluorene Derivative that Behaves as an Efficient Blue-Light Emitter in Organic Light-Emitting Diodes" Org. Lett. 2007, 9, 4511-4514. (Year: 2007).*
Liao et al. "Hole Mobilities of 2,7- and 2,2'-Disubstituted 9,9'-Spirobifluorene-Based Triaryldiamines and Their Application as Hole Transport Materials in OLEDs" Chem. Mater. 2007, 19, 6350-6357. (Year: 2007).*

(Continued)

*Primary Examiner* — Robert S Loewe

(74) *Attorney, Agent, or Firm* — Alston & Bird LLP

(57) ABSTRACT

Provided are a light-emitting element and a display device containing the light-emitting element. The light-emitting element comprises an anode, a cathode opposite to the anode, and a plurality of organic layers placed between the anode and the cathode; at least three of the plurality of organic layers each independently contain a compound having a spirobifluorene structure; or at least two of the plurality of organic layers each contain the compound having a spirobifluorene structure and together contain at least three types of the compound having a spirobifluorene structure. By providing the organic layers with the compound having a spirobifluorene structure, the HOMO or LUMO energy level difference for hole or electron transport between different organic layers can be reduced due to the spirobifluorene compounds having the same main ring structure, which facilitates injection of electrons and/or holes, improving the luminous efficiency and lowering the turn on voltage.

17 Claims, 3 Drawing Sheets

(56) References Cited

U.S. PATENT DOCUMENTS

| | | | | |
|---|---|---|---|---|
| 2014/0225040 A1* | 8/2014 | Parham | ............... | C07D 209/96 |
| | | | | 252/500 |
| 2015/0065730 A1* | 3/2015 | Montenegro | ........ | C07D 209/88 |
| | | | | 548/440 |
| 2015/0236261 A1* | 8/2015 | Stoessel | ................ | H05B 33/22 |
| | | | | 257/40 |
| 2015/0255520 A1* | 9/2015 | Seo | .................... | H01L 51/5215 |
| | | | | 257/89 |
| 2016/0285003 A1* | 9/2016 | Gaudin | ............. | H01L 51/0058 |
| 2016/0365529 A1* | 12/2016 | Kim | ................... | H01L 51/5092 |
| 2017/0237017 A1* | 8/2017 | Parham | ............. | H01L 51/0059 |
| | | | | 252/500 |
| 2018/0026188 A1* | 1/2018 | Pfister | ................. | C07D 307/94 |
| | | | | 257/40 |
| 2018/0145272 A1* | 5/2018 | Cha | ........................ | H01L 51/50 |
| 2018/0269400 A1* | 9/2018 | Jatsch | ................ | C07D 491/04 |
| 2019/0051835 A1* | 2/2019 | Takahashi | ............ | C07D 237/08 |
| 2019/0067576 A1* | 2/2019 | Voges | ..................... | C07C 17/35 |
| 2019/0106391 A1* | 4/2019 | Wucherer-Plietker | ...................... | C07D 403/04 |
| 2020/0140440 A1* | 5/2020 | Jatsch | .................... | A61P 43/00 |

FOREIGN PATENT DOCUMENTS

| | | |
|---|---|---|
| CN | 102627522 A | 8/2012 |
| CN | 103108859 A | 5/2013 |
| CN | 105237501 A | 1/2016 |
| TW | 201533010 A | 9/2015 |

OTHER PUBLICATIONS

CN Application No. 201710692601.7, 1st Office Action dated Aug. 28, 2018.

* cited by examiner

LIGHT-EMITTING ELEMENT AND DISPLAY DEVICE

CROSS-REFERENCE TO RELATED APPLICATIONS

The present disclosure claims priority to Chinese Patent Application No. 201710692601.7, filed on Aug. 14, 2017, the content of which is incorporated herein by reference in its entirety.

TECHNICAL FIELD

The present disclosure relates to the field of organic light-emitting display technologies and, particularly, to a light-emitting element and a display device.

BACKGROUND

With the advent of the information age, the conventional cathode-ray tube (CRT) displays are being replaced by the flat panel displays. A liquid crystal display (LCD), as one of the most widely used panel displays, has characteristics of low power consumption and light weight. However, since LCDs are unable to emit light by themselves, there are technical limitations on the aspects of contrast, visual angle, area and size. An organic light-emitting diode (OLED) has attracted much attention due to its characteristics of self-illumination, wide visual angle, short response time, high luminous efficiency, wide color gamut, low working voltage, thin panel, and an applicability for producing large-size and bendable displays.

In the existing OLED display devices, the main light-emitting unit is consisting of an anode, a cathode and a series of organic layers placed between the anode and the cathode. The organic layers are generally divided according to their functions and include a hole injection layer (HIL), a hole transport layer (HTL), an electron transport layer (ETL) and an electron injection layer (EIL), and some devices may further include a hole blocking layer (HBL) and an electron blocking layer (EBL), depending on requirements.

The electron transport rate of most organic materials is far smaller than that of the hole transport rate. Therefore, it has been one of the focuses of researches to find a transport material or a barrier material, which can balance the electron transport rate and the hole transport rate, and to develop a structure, which can meet other conditions, improve its efficiency and lower the voltage.

SUMMARY

In view of the above, the present disclosure provides a light-emitting element and a display device.

In one aspect, the present disclosure provides a light-emitting element including an anode, a cathode placed opposite to the anode, and a plurality of organic layers placed between the anode and the cathode, wherein at least three of the plurality of organic layers each independently contain a compound having a spirobifluorene structure; or at least two of the plurality of organic layers each contain the compound having a spirobifluorene structure, and the at least two organic layers together contain at least three types of the compound having a spirobifluorene structure.

In another aspect, the present disclosure provides a display device, including the light-emitting element according to the first aspect of the present disclosure.

BRIEF DESCRIPTION OF DRAWINGS

In order to clearly illustrate the technical solutions of the embodiments of the present disclosure, drawings used in the embodiments are briefly described as follows. Obviously, the drawings described below are merely a part of embodiments of the present disclosure, based on which the person skilled in the art can easily derive other drawings without creative working.

REFERENCE SIGNS

Figure 1:
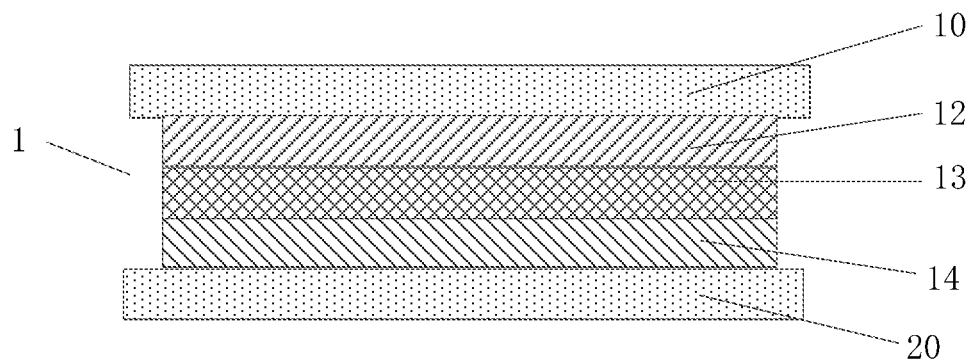
FIG. 1 is a structural schematic diagram of a light-emitting element according to an embodiment of the present disclosure.

1—light-emitting element;
  10—anode;
  11—hole injection layer;
  12—hole transport layer;
  13—light-emitting layer;
  14—electron transport layer;
  15—electron injection layer;
  16—hole blocking layer;
  17—electron blocking layer;
  20—cathode.

DESCRIPTION OF EMBODIMENTS

The embodiments of the present disclosure is described in detail below with reference to the accompanying drawings, in order to better understand the technical solutions of the present disclosure.

It should be appreciated that the described embodiments are only a part of the embodiments of the present disclosure, but not all of the embodiments. Other embodiments, which can be derived by the person skilled in the art on the basis of the embodiments in the present disclosure without creative working, also fall into the protection scope of the present disclosure.

The terms used in the embodiments of the present disclosure aim to describe the specific embodiments of the present disclosure and, are not intended to limit the present disclosure. In the embodiments of the invention and the appended claims, the singular forms such as "a", "one" and "the" are also intended to include the plural forms thereof, unless otherwise noted.

The embodiments of the present disclosure provide a light-emitting element. as shown in FIGS. 1-5, the light-emitting element 1 comprises an anode 10, a cathode 20 placed opposite to the anode 10, and a plurality of organic layers placed between the anode 10 and the cathode 20.

The plurality of organic layers of the light-emitting element according to the embodiments of the present disclosure may include at least three layers. For example, the plurality of organic layers of the light-emitting element according to the embodiments of the present disclosure may include three layers, for example, a hole transport layer, a light-emitting layer and an electron transport layer. Or, the plurality of organic layers of the light-emitting element may include four layers, for example, a hole injection layer, a hole transport layer, a light-emitting layer and an electron transport layer, or a hole transport layer, a light-emitting layer, an electron transport layer and an electron injection layer. Or, the plurality of organic layers of the light-emitting element may include five layers, for example, a hole injection layer, a hole transport layer, a light-emitting layer, an electron transport layer and an electron injection layer. Optionally, the plurality of organic layers of the light-emitting element, according to the embodiments of the present disclosure, may include six or seven layers. In the above-described organic layers of the light-emitting element, at least three of the plurality of organic layers each independently contain a compound having a spirobifluorene structure; or at least two of the plurality of organic layers each contain the compound having a spirobifluorene structure, and the at least two organic layers together contain at least three types of the compound having a spirobifluorene structure. The three types of the compound having a spirobifluorene structure refer to three types of spirobifluorene compounds having different chemical structural formulas with different substituent groups.

As shown in FIG. 1, the plurality of organic layers of the light-emitting element 1 according to an embodiment of the present disclosure include a hole transport layer 12, a light-emitting layer 13 and an electron transport layer 14, and the hole transport layer 12, the light-emitting layer 13 and the electron transport layer 14 are sequentially arranged from the anode 10 to the cathode 20.

Figure 2:
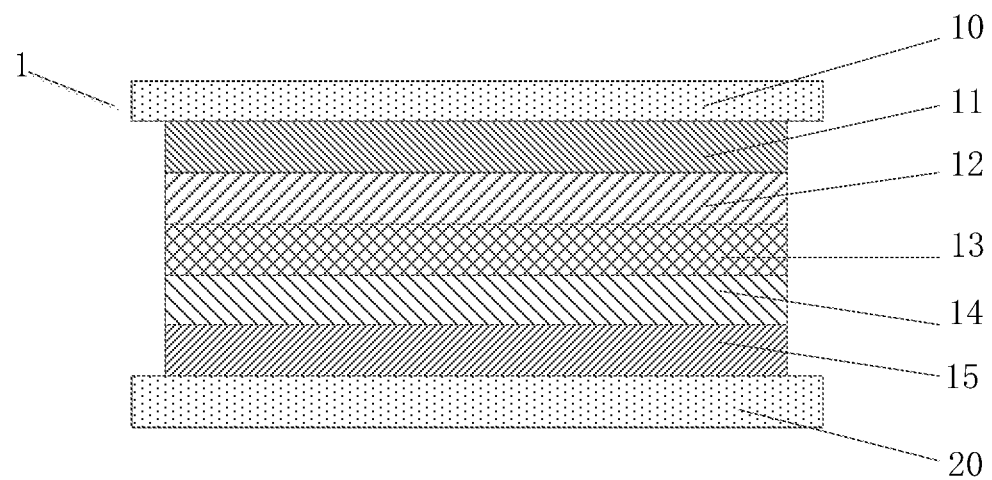
FIG. 2 is a structural schematic diagram of another light-emitting element according to an embodiment of the present disclosure.

As shown in FIG. 2, the plurality of organic layers of the light-emitting element 1 according to another embodiment of the present disclosure include a hole injection layer 11, a hole transport layer 12, a light-emitting layer 13, an electron transport layer 14, and an electron injection layer 15, and the hole injection layer 11, the hole transport layer 12, the light-emitting layer 13, the electron transport layer 14, and the electron injection layer 15 are sequentially arranged from the anode 10 to the cathode 20.

Figure 3:
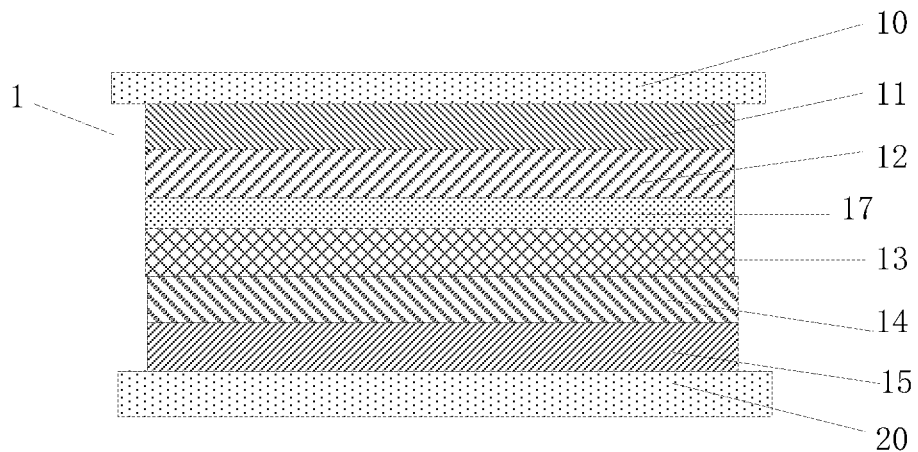
FIG. 3 is a structural schematic diagram of still another light-emitting element according to an embodiment of the present disclosure.

As shown in FIG. 3, the plurality of organic layers of the light-emitting element 1 according to still another embodiment of the present disclosure include a hole injection layer 11, a hole transport layer 12, an electron blocking layer 17, a light-emitting layer 13, an electron transport layer 14, and an electron injection layer 15, and the hole injection layer 11, the hole transport layer 12, the electron blocking layer 17, the light-emitting layer 13, the electron transport layer 14, and the electron injection layer 15 are sequentially arranged from the anode 10 to the cathode 20.

Figure 4:
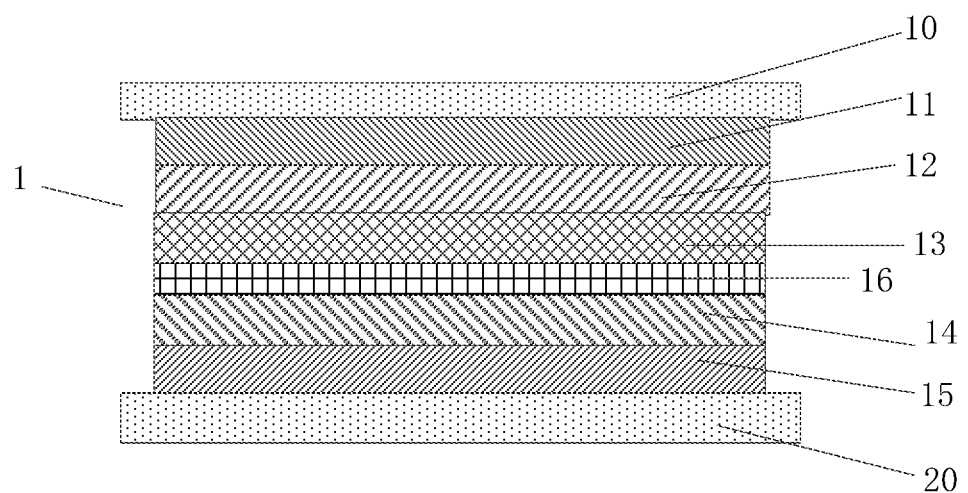
FIG. 4 is a structural schematic diagram of still another light-emitting element according to an embodiment of the present disclosure.

As shown in FIG. 4, the plurality of organic layers of the light-emitting element 1 according to still another embodiment of the present disclosure include a hole injection layer 11, a hole transport layer 12, a light-emitting layer 13, a hole blocking layer 16, an electron transport layer 14, and an electron injection layer 15, and the hole injection layer 11, the hole transport layer 12, the light-emitting layer 13, the hole blocking layer 16, the electron transport layer 14, and the electron injection layer 15 are sequentially arranged from the anode 10 to the cathode 20.

Figure 5:
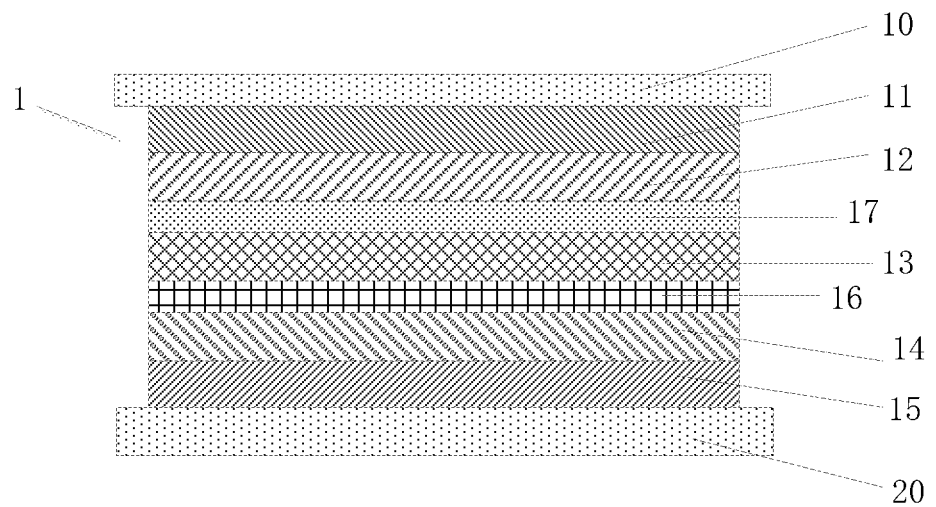
FIG. 5 is a structural schematic diagram of still another light-emitting element according to an embodiment of the present disclosure.

As shown in FIG. 5, the plurality of organic layers of the light-emitting element 1 according to still another embodiment of the present disclosure include a hole injection layer 11, a hole transport layer 12, an electron blocking layer 17, a light-emitting layer 13, a hole blocking layer 16, an electron transport layer 14, and an electron injection layer 15, and the hole injection layer 11, the hole transport layer 12, the electron blocking layer 17, the light-emitting layer 13, the hole blocking layer 16, the electron transport layer 14, and the electron injection layer 15 are sequentially arranged from the anode 10 to the cathode 20.

In the embodiments of the present disclosure, at least three of the plurality of organic layers contain a same or different spirobifluorene compound(s), or at least two of the plurality of organic layers contain at least three types of compounds having a spirobifluorene structure. Since these spirobifluorene compounds have a same main ring structure, the HOMO or LUMO energy level difference for hole or electron transport between different organic layers can be reduced, which facilitates the injection of electrons and/or holes, thereby improving the luminous efficiency and lowering the turn on voltage. For example, when the hole transport layer, the hole injection layer and the light-emitting layer all contain compound(s) having a spirobifluorene structure, the HOMO energy level difference between any two of these three layers can be reduced, and the holes are more easily transported to the light-emitting layer. For example, when the electron injection layer, the electron transport layer and the light-emitting layer all contain compound(s) having a spirobifluorene structure, the LUMO energy level difference between any two of these three layers can be reduced, and the electrons are more easily transported to the light-emitting layer. For example, when the electron transport layer, the light-emitting layer and the hole transport layer all contain compound(s) having a spirobifluorene structure, the HOMO energy level difference between the hole transport layer and the light-emitting layer can be reduced so that the holes are more easily transported to the light-emitting layer, and the LUMO energy level difference between the electron transport layer and the light-emitting layer can also be reduced so that the electrons are more easily transported to the light-emitting layer. However, if the same or different spirobifluorene compound(s) is provided in only two organic layers, the reduction of the HOMO or LUMO energy level difference for hole or electron transport between different organic layers will not be significant for the whole light-emitting element, and the improvement of the luminous efficiency will beunobvious.

In the above-described organic layers containing the spirobifluorene compound, each organic layer can be formed by directly depositing a spirobifluorene compound or by doping the spirobifluorene compound. In order to improve the technical effects of the light-emitting elements as described in the above embodiments of the present disclosure, in the organic layer doped with the spirobifluorene compound, the content of the spirobifluorene compound should be more than 30 wt %, optionally more than 50 wt %. In the case that the requirements on the energy level are satisfied, the higher the doping amount of the spirobifluorene compounds is, the more remarkable the above-mentioned technical effects are. Thus, the person skilled in the art can select the amount of the spirobifluorene compound, according to the specific requirements on the light-emitting element.

Optionally, the at least three of the plurality of organic layers each containing the spirobifluorene compound are sequentially stacked to constitute a continuous transport path for holes and/or electrons; or the at least two of the plurality of organic layers containing the spirobifluorene compound are sequentially stacked to constitute a continuous transport path for holes and/or electrons. In an instance in which two organic layers contain the spirobifluorene compound, at least one of the two organic layers contains two different spirobifluorene compounds. Optionally, the light-emitting layer according to an embodiment of the present disclosure may contain two spirobifluorene compounds, as a host material and a doping material, respectively.

Optionally, a glass transition temperature Tg of the compound having a spirobifluorene structure is greater than or equal to 120° C., so that the luminous efficiency of the element can be improved.

In the embodiments of the present disclosure, the compound having a spirobifluorene structure can be selected from a group consisting of compounds represented by formula I and combinations thereof;

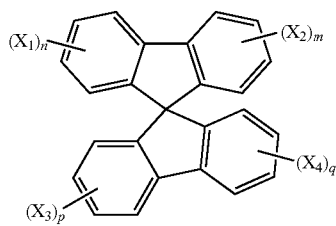

(I)

wherein $X_1$, $X_2$, $X_3$, and $X_4$ are independently selected from a group consisting of hydrogen atom, an electron donating group and an electron withdrawing group;

n, m, p, and q are integers independently selected from a group consisting of 1, 2, 3 and 4.

When substituents are fused to benzene rings of a compound having a spirobifluorene structure to form a fused compound having the spirobifluorene structure, the fused compound having the spirobifluorene structure is selected from a group consisting of compounds represented by a formula II and combinations thereof;

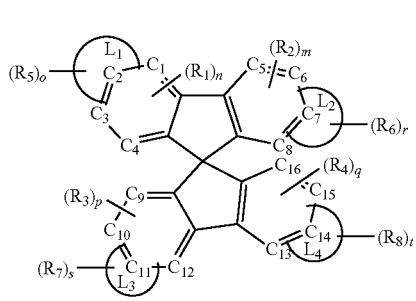

(II)

wherein at least one of ring structure $L_1$, ring structure $L_2$, ring structure $L_3$ and ring structure $L_4$ is present in the general formula II and is independently an aromatic ring having 6-42 carbon atoms;

when the ring structure $L_1$ is present in the general formula II, the ring structure $L_1$ is fused to $C_1$ and $C_2$, $C_2$ and $C_3$, or $C_3$ and $C_4$;

when the ring structure $L_2$ is present in the general formula II, the ring structure $L_2$ is fused to $C_5$ and $C_6$, $C_6$ and $C_7$, or $C_7$ and $C_8$;

when the ring structure $L_3$ is present in the general formula II, the ring structure $L_3$ is fused to $C_9$ and $C_{10}$, $C_{10}$ and $C_{11}$, or $C_{11}$ and Cu;

when the ring structure $L_4$ is present in the general formula II, the ring structure $L_4$ is fused to $C_{13}$ and $C_{14}$, $C_{14}$ and $C_{15}$, or $C_{15}$ and $C_{16}$, $R_1$, $R_2$, $R_3$, $R_4$, $R_5$, $R_6$, $R_7$, and $R_8$ are independently selected from a group consisting of hydrogen atom, an electron donating group and an electron withdrawing group; and n, m, p, q, o, r, s, and t are integers independently selected from a group consisting of 1, 2, 3, and 4.

In the above formula I and formula II, the electron withdrawing group is selected from a group consisting of halogen atom, nitro, cyano, $C_1$-$C_{40}$ alkyl unsubstituted or substituted with a substituent, $C_6$-$C_{60}$ arylamine unsubstituted or substituted with a substituent, $C_6$-$C_{60}$ heteroarylamine unsubstituted or substituted with a substituent, $C_3$-$C_{60}$ heteroaryl unsubstituted or substituted with a substituent, $C_6$-$C_{60}$ aryl substituted with a substituent, and combinations thereof, wherein the substituent is selected from a group consisting of halogen atom, nitro and cyano.

In the above formula I and formula II, the electron donating group is selected from a group consisting of hydroxyl, $C_1$-$C_{40}$ alkoxy unsubstituted or substituted with a substituent, $C_1$-$C_{40}$ alkyl unsubstituted or substituted with a substituent, $C_6$-$C_{60}$ aryl unsubstituted or substituted with a substituent, and combinations thereof, wherein the substituent is hydroxyl.

Optionally, the aryl is selected from a group consisting of phenyl, naphthyl, phenanthryl, fluorenyl, and biphenyl.

Optionally, the heteroaryl is selected from a group consisting of furyl, thienyl, pyrrolyl, thiazolyl, imidazolyl, pyridyl, pyrazinyl, pyrimidinyl, pyridazinyl, indolyl, quinolyl, carbazolyl, benzopyrrolyl, benzopyridyl, dibenzofuryl, dibenzothienyl, diphenyltriazinyl, and dipyridyl.

Optionally, in the above formula I and formula II, the electron withdrawing group is selected from a group consisting of groups represented by structural formulas shown as below:

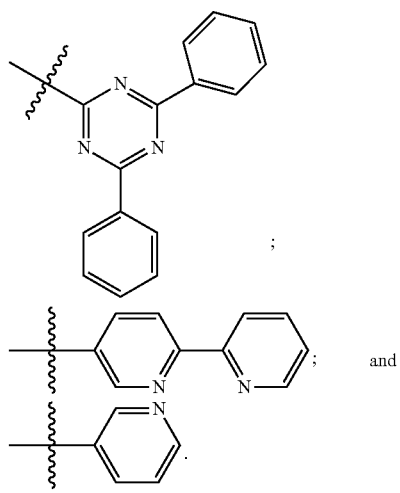

Optionally, in the above formula I and formula II, the electron donating group is selected from a group consisting of groups represented by structural formulas shown as below:

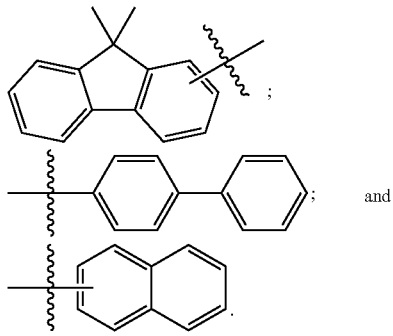

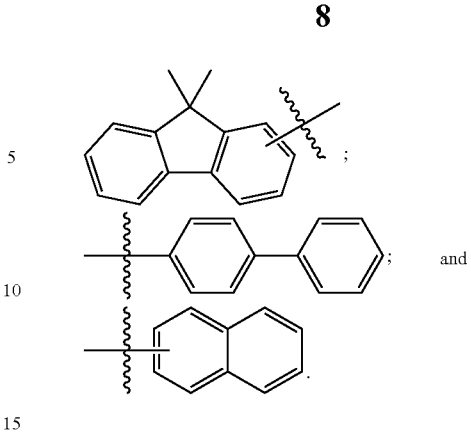

In the present disclosure, by selecting the substituents on the compounds having spirobifluorene structure in the organic layers, the hole transport property or the electron transport property of the spirobifluorene compound can be regulated and controlled so as to form a collocation of materials having same main ring while satisfying electron and/or hole transport properties. Thus, the hole transport property or the electron transport property of the different organic layers containing the above-described spirobifluorene compound can be regulated and controlled, facilitating the injection of electrons and/or holes of the light-emitting element, and increasing the luminous efficiency of the light-emitting element and lowering the turn on voltage.

When at least one layer with electron transport property (electron injection layer, electron transport layer and hole blocking layer) independently contains a compound having spirobifluorene structure, the electron mobility of the compound is greater than the hole mobility of the compound; namely, $X_1$, $X_2$, $X_3$, and $X_4$ in the general formula I are independently selected from a group consisting of hydrogen atom and an electron donating group.

The LUMO energy level difference between the electron injection layer and the electron transport layer should be less than or equal to 0.3 eV. Therefore, if both the electron injection layer and the electron transport layer are made of the spirobifluorene compound, the selected compound for making the electron injection layer and the selected compound for making the electron transport layer should be different from one another while satisfying the above-described requirements on energy level difference.

Different layers of the electron injection layer, the electron transport layer and the hole blocking layer can contain the same spirobiluorene compound. For example, when the electron transport layer and the hole blocking layer contain the same spirobiluorene compound, the same compound having a spirobifluorene structure is present in at least one of the electron transport layer and the hole blocking layer in a doping form, forming a LUMO energy level difference for facilitating electron transport. Furthermore, a doping percentage should be no less than 30%, optionally no less than 50%, thereby further reducing the interface resistance, and improving the transport performance of electrons.

Optionally, in the layers with electron transport property, the electron donating group is selected from a group consisting of the following groups:

When at least one of the layers with hole transport property (hole injection layer, hole transport layer and electron blocking layer) independently contains the compound spirobifluorene compound, the hole mobility of the spirobifluorene compound is greater than the electron mobility of the spirobifluorene compound; namely, in the general formula I, $X_1$, $X_2$, $X_3$, and $X_4$ are independently selected from a group consisting of hydrogen atom and an electron withdrawing group, and at least one of $X_1$, $X_2$, $X_3$, and $X_4$ is an electron withdrawing group, wherein the electron withdrawing group can be selected from the above-exemplified substituents.

The HOMO energy level difference between the hole injection layer and the hole transport layer should be less than or equal to 0.3 eV. Therefore, if both the hole injection layer and the hole transport layer are made of the spirobifluorene compound, the selected spirobifluorene compound for making the hole injection layer and the selected spirobifluorene compound for making the hole transport layer should be different from each other while satisfying the above-mentioned requirements on energy level difference. However, different layers of the hole injection layer, the hole transport layer and the electron blocking layer can contain a same spirobiluorene compound. For example, the hole injection layer and the electron blocking layer contain the same spirobiluorene compound, the same spirobifluorene compound in at least one of the hole injection layer and the electron blocking layer is present in a doping form, forming a HOMO energy level difference for facilitating hole transport. Furthermore, a doping proportion should be no less than 30%, optionally no less than 50%, thereby further reducing the interface resistance and improving the hole transport performance.

Optionally, in the layers with hole transport property, the electron withdrawing group is selected from a group consisting of the following groups:

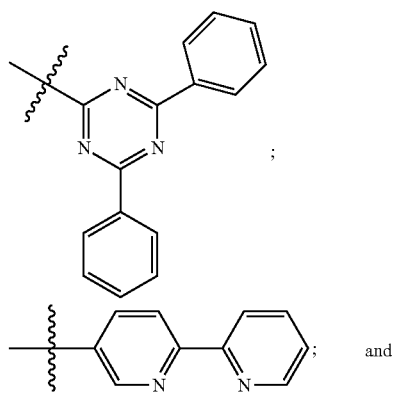

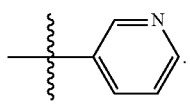

When at least one host material and at least one doping material in the light-emitting layer independently contain the spirobifluorene compound:

When the host material contains the spirobifluorene compound, as represented by the general formula I, at least one of $X_1$, $X_2$, $X_3$, and $X_4$ should be selected from electron withdrawing groups, as the host material is required to have both an ability of transporting electrons and an ability of transport holes.

When the doping material contains the spirobifluorene compound, the doping material is only required to have the ability of transporting holes. For example, if the spirobifluorene compounds represented by the general formula I have the ability of transporting hole, $X_1$, $X_2$, $X_3$, and $X_4$ can be hydrogen atom, or each independently selected from electron donating groups; if the spirobifluorene compounds represented by the general formula II also the ability of transport holes, $R_1$, $R_2$, $R_3$, $R_4$, $R_5$, $R_6$, $R_7$, and $R_8$ are independently selected from a group consisting of hydrogen atom and electron donating group.

In an embodiment of the present disclosure, the light-emitting layer can contain two spirobifluorene compounds, as a host material and a doping material, respectively. The non-planar structure of the spirobifluorene compounds can effectively inhibit the accumulation of the material, and the spirobifluorene compounds also have advantages of high thermal stability, high luminous efficiency, high color purity, etc. Therefore, the luminous efficiency and color purity of the light-emitting element can be effectively improved, when different spirobifluorene compounds are used as the host materials and the doping material.

Figure 6:
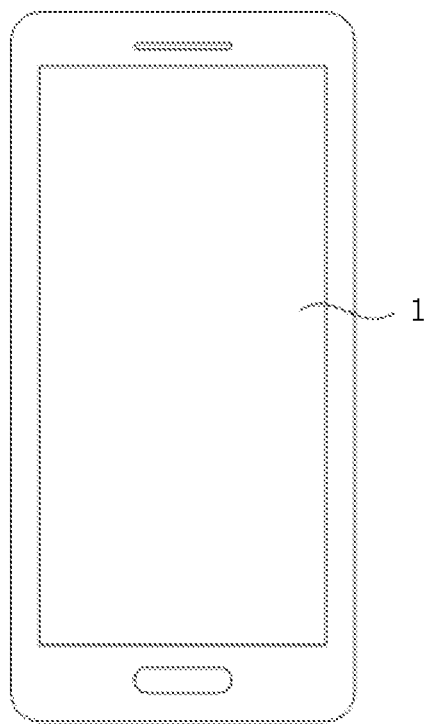
FIG. 6 is a structural schematic diagram of a display device according to an embodiment of the present disclosure.

A second aspect of the embodiments of the present disclosure provides a display device. As shown in FIG. 6, the display device comprises the light-emitting element 1 according to the first aspect of the embodiments of the present disclosure. The display device can be any electronic device having a function of displaying such as a touch screen, a mobile phone, a tablet computer, a notebook computer, an e-book, a television set, etc.

In the following, the embodiments of the present disclosure are explained in a more detailed way. In the following specific embodiments, the following exemplary spirobifluorene compounds can be selected, and these compounds are not intended to limit the scope of the embodiments of the present disclosure. On the basis of the context of the present disclosure, the person skilled in the art is able to choose other spirobifluorene compounds for achieving the effects of the light-emitting element according to the embodiments of the present disclosure.

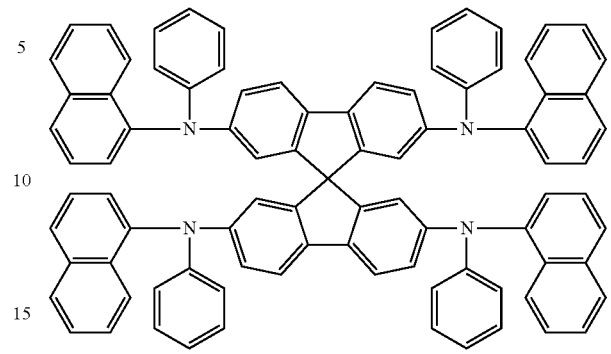
(Formula 1)

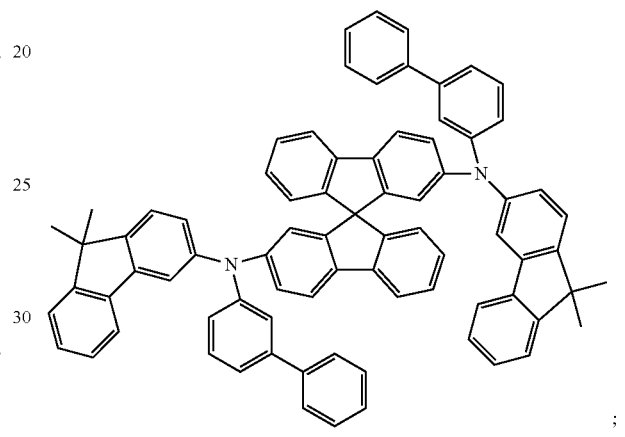
(Formula 2)

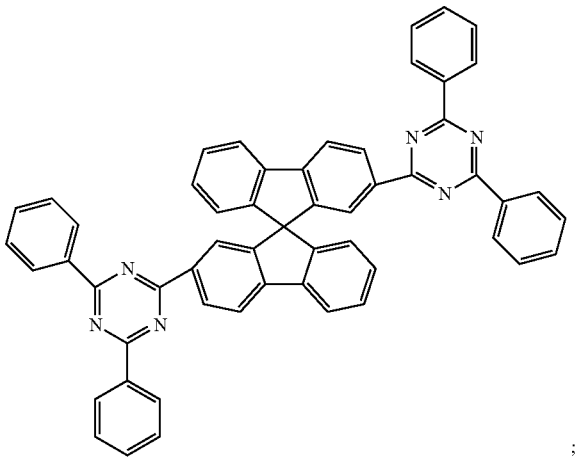
(Formula 3)

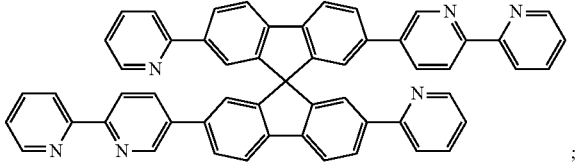
(Formula 4)

(Formula 5)

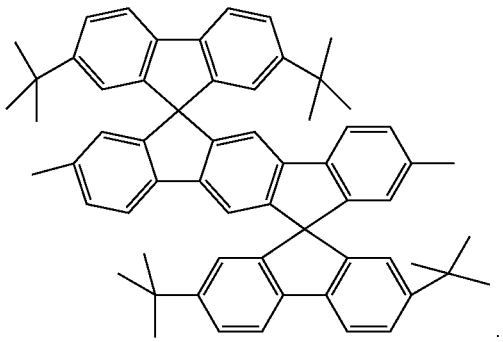

Embodiment 1

In the present embodiment, the layer mainly for transporting holes, the light-emitting layer, and the layer mainly for transporting electrons can contain the spirobifluorene compound, thereby improving the injection of both electrons and holes, improving the luminous efficiency and lowering the turn on voltage.

In other words, at least one of the hole injection layer, the hole transport layer and the electron blocking layer independently contains the spirobifluorene compound, the light-emitting layer contains the spirobifluorene compound, and at least one of the electron injection layer, the electron transport layer and the hole blocking layer independently contains the spirobifluorene compound.

As an example, in the light-emitting element with five organic layers shown in FIG. 2, the hole injection layer 11, the hole transport layer 12, the light-emitting layer 13, and the electron transport layer 14 all contain the spirobifluorene compound.

When the four layers described above all contain the spirobifluorene compound, the spirobifluorene compound used in each layer should satisfy: the LUMO energy level difference between the electron transport layer and the light-emitting layer is less than or equal to 0.3 eV; the LUMO energy level difference between the light-emitting layer and the hole transport layer is greater than or equal to 0.3 eV; the HOMO energy level difference between every two adjacent layers of the hole injection layer, the hole transport layer and the light-emitting layer is less than or equal to 0.3 eV; the HOMO energy level difference between the light-emitting layer and the electron transport layer is greater than or equal to 0.3 eV, for meeting the requirements of carrier injection.

The appropriate spirobifluorene compounds for producing the light-emitting element is selected according to the LUMO-HOMO energy level data disclosed in the technical manual. The spirobifluorene compounds used in the layers of the light-emitting element are exemplarily shown in Table 1.

TABLE 1

| Organic layer | Light-emitting element 1# | Light-emitting element 2# |
|---|---|---|
| Hole injection layer | Formula 1 | Formula 1 |
| Hole transport layer | Formula 2 | Formula 2 |
| Light-emitting layer | Formula 3 as host material, Formula 4 as doping material | Formula 3 as host material |
| Electron transport layer | Formula 5 | Formula 5 |

In the above-described light-emitting elements, the electron injection layer can also contain the spirobifluorene compound, and the LUMO energy level difference between the electron injection layer and the electron transport layer should be less than or equal to 0.3 eV.

As an example, in the light-emitting element with six organic layers shown in FIG. 3, on the basis of the above-mentioned light-emitting element, the spirobifluorene compound represented by Formula 1 can be doped into the electron blocking layer 17.

As an example, in the light-emitting element with six organic layers shown in FIG. 4, on the basis of the above-mentioned light-emitting element, the spirobifluorene compound represented by Formula 5 can be doped into the hole blocking layer 16.

As an example, in the light-emitting element with seven organic layers shown in FIG. 5, on the basis of the above-mentioned light-emitting element, the spirobifluorene compounds can be doped into the electron blocking layer 17 and the hole blocking layer 16. The spirobifluorene compound represented by Formula 5 can be doped into the hole blocking layer 16, while the spirobifluorene compound represented by Formula 1 can be doped into the electron blocking layer 17.

Embodiment 2

For example, in the light-emitting element with three organic layer shown in FIG. 1, the hole transport layer 12, the light-emitting layer 13 and the electron transport layer 14 contain the spirobifluorene compound.

When the three layers described above all contain the spirobifluorene compound, the spirobifluorene compound used in each layer should satisfy: the LUMO energy level difference between the electron transport layer and the light-emitting layer is less than or equal to 0.3 eV; the LUMO energy level difference between the light-emitting layer and the hole transport layer is greater than or equal to 0.3 eV; the HOMO energy level difference between the hole transport layer and the light-emitting layer is less than or equal to 0.3 eV; and the HOMO energy level difference between the light-emitting layer and the electron transport layer is greater than or equal to 0.3 eV, for meeting the requirements of carrier injection.

The appropriate spirobifluorene compounds for producing the light-emitting element can be selected according to the LUMO-HOMO energy level data disclosed in the technical manual.

The spirobifluorene compounds used in the layers of the light-emitting element are exemplarily shown in Table 2.

TABLE 2

| Organic layer | Light-emitting element 3# | Light-emitting element 4# |
|---|---|---|
| Hole transport layer | Formula 2 | Formula 2 |
| Light-emitting layer | Formula 3 as host material, Formula 4 as doping material | Formula 3 as host material |
| Electron transport layer | Formula 5 | Formula 5 |

In the above-described light-emitting elements, the electron injection layer can also contain the spirobifluorene compound, and the LUMO energy level difference between the electron injection layer and the electron transport layer should be less than or equal to 0.3 eV. As an example, in the light-emitting element with six organic layers shown in FIG. 3, on the basis of the above-mentioned light-emitting element, the spirobifluorene compound represented by Formula 1 is doped into the electron blocking layer 17.

As an example, in the light-emitting element with six organic layers shown in FIG. 4, on the basis of the above-mentioned light-emitting element, the spirobifluorene compound represented by Formula 5 is doped into the hole blocking layer 16.

As an example, in the light-emitting element with seven organic layers shown in FIG. 5, on the basis of the above-mentioned light-emitting element, the spirobifluorene compound can be doped into the electron blocking layer 17 and the hole blocking layer 16.

The spirobifluorene compound represented by Formula 5 can be doped into the hole blocking layer 16, while the spirobifluorene compound shown by Formula 1 can be doped into the electron blocking layer 17.

Embodiment 3

In the present embodiment of the present disclosure, the layer mainly for transporting holes and the light-emitting layer can contain the spirobifluorene compounds. In other words, at least one of the hole injection layer, the hole transport layer and the electron blocking layer independently contains the spirobifluorene compound, and the light-emitting layer contains the spirobifluorene compound.

As an example, in the light-emitting element with three organic layers shown in FIG. 1, both the hole transport layer 12 and the light-emitting layer 13 contain the spirobifluorene compound; and the light-emitting layer 13 contains two different spirobifluorene compounds.

When the two layers described above both contain the spirobifluorene compound, the spirobifluorene compound used in each layer should satisfy: the LUMO energy level difference between the light-emitting layer and the hole transport layer is greater than or equal to 0.3 eV; and the HOMO energy level difference between the hole transport layer and the light-emitting layer is less than or equal to 0.3 eV, for meeting the requirements of carrier injection.

The appropriate spirobifluorene compounds for producing the light-emitting element can be selected according to the LUMO-HOMO energy level data disclosed in the technical manual. The spirobifluorene compounds used in the layers of the light-emitting element are exemplarily shown in Table 3.

TABLE 3

| Organic layer | Light-emitting element 5# |
|---|---|
| Hole transport layer | Formula 2 |
| Light-emitting layer | Formula 3 as host material, Formula 4 as doping material |

As an example, in the light-emitting element with six organic layers shown in FIG. 3, on the basis of the above-mentioned light-emitting element, the spirobifluorene compound shown by Formula 1 can be doped into the electron blocking layer 17.

Embodiment 4

As an example, in the light-emitting element with five organic layers shown in FIG. 2, the hole injection layer 11, the hole transport layer 12 and the light-emitting layer 13 contain the spirobifluorene compounds.

When the three layers described above all contain the spirobifluorene compound, the spirobifluorene compound used in each layer should satisfy: the LUMO energy level difference between the light-emitting layer and the hole transport layer is greater than or equal to 0.3 eV; and the HOMO energy level difference between every two adjacent layers of the hole injection layer, the hole transport layer and the light-emitting layer is less than or equal to 0.3 eV, for meeting the requirements of carrier injection.

The appropriate spirobifluorene compounds for producing the light-emitting element can be selected according to the LUMO-HOMO energy level data disclosed in the technical manual. The spirobifluorene compounds used in the layers of the light-emitting element are exemplarily shown in Table 4.

TABLE 4

| Organic layer | Light-emitting element 6# | Light-emitting element 7# |
|---|---|---|
| Hole injection layer | Formula 1 | Formula 1 |
| Hole transport layer | Formula 2 | Formula 2 |
| Light-emitting layer | Formula 3 as host material, Formula 4 as doping material | Formula 3 as host material |

As an example, in the light-emitting element with six organic layers shown in FIG. 3, on the basis of the above-mentioned light-emitting element, the spirobifluorene compound represented by Formula 1 can be doped into the electron blocking layer 17.

As an example, in the light-emitting element with seven organic layers shown in FIG. 5, on the basis of the above-mentioned light-emitting element, the spirobifluorene compound represented by Formula 1 can be doped into the electron blocking layer 17.

Embodiment 5

In the present embodiment, the electron injection layer, the electron transport layer, and the light-emitting layer can contain the spirobifluorene compound. Optionally, the electron transport layer and the light-emitting layer contain the spirobifluorene compound, and the light-emitting layer contain two different spirobifluorene compounds.

As an example, in the light-emitting element with five organic layers shown in FIG. 1, the hole injection layer 11, the hole transport layer 12 and the light-emitting layer 13 contain the spirobifluorene compound, and the light-emitting layer contain two different spirobifluorene compounds.

When the electron transport layer and the light-emitting layer described above all contain the spirobifluorene compound, the spirobifluorene compound used in each layer should satisfy: the LUMO energy level difference between the electron transport layer and the light-emitting layer is less than or equal to 0.3 eV; and the HOMO energy level difference between the light-emitting layer and the electron transport layer is greater than or equal to 0.3 eV, for meeting the requirements of carrier injection.

The appropriate spirobifluorene compounds for producing the light-emitting element can be selected according to the LUMO-HOMO energy level data disclosed in the technical manual. The spirobifluorene compounds used in the layers of the light-emitting element are exemplarily shown in Table 5.

TABLE 5

| Organic layers | Light-emitting element 8# |
| --- | --- |
| Light-emitting layer | Formula 3 as host material, formula 4 as doping material |
| Electron transport layer | Formula 5 |

In the above-described light-emitting element, the electron injection layer can also contain the spirobifluorene compound, and the LUMO energy level difference between the electron injection layer and the electron transport layer should be less than or equal to 0.3 eV.

As an example, in the light-emitting element with six organic layers shown in FIG. 4, on the basis of the above-mentioned light-emitting element, the spirobifluorene compound represented by Formula 5 can be doped into the hole blocking layer 16.

As an example, in the seven organic layers shown in FIG. 5, on the basis of the above-mentioned light-emitting element, the spirobifluorene compound represented by Formula 5 can be doped into the hole blocking layer 16.

Performance evaluation of light-emitting elements according to the embodiments of the present disclosure are describe as follows:

Preparation of OLED element: preparing a TFT substrate; forming an anode on the TFT substrate; forming the organic layers containing spirobifluorene compounds on the anode; and forming a cathode.

Light-emitting elements are produced according to the collocations of materials in the above-described embodiments. Taking the bottom emission type structure which emits blue light as an example, the elements are structured as follows:

Light-emitting element 1#: ITO (100 nm)/Formula 1 (60 nm)/Formula 2 (10 nm)/Formula 3: Formula 4 (95 wt %: 5 wt %, 30 nm)/Formula 5 (20 nm)/LiF (1 nm)/Al (100 nm);

In Light-emitting element 1, ITO represents the anode, and the size in parentheses indicates the thickness, for example, ITO (100 nm) indicates that the thickness of the anode is 100 nm; the general formula 1 is a hole injection layer with a thickness of 60 nm; Formula 2 is a hole transport layer with a thickness of 10 nm; Formula 3 is a host material, and Formula 4 is a doping material, wherein 5 wt % indicates the doping mass percentage in the doping material; the general formula 5 is an electron transport layer with a thickness of 20 nm; LiF represents an electron injection layer with a thickness of 1 nm; and Al represents a cathode electrode with a thickness of 100 nm.

Light-emitting element 2#: ITO (100 nm)/Formula 1 (60 nm)/Formula 2 (10 nm)/formula 3: DPAVB (95 wt %:5 wt %, 30 nm)/Formula 5 (20 nm)/LiF (1 nm)/Al (100 nm);

Light-emitting element 3#: ITO (100 nm)/NPD (60 nm)/Formula 2 (10 nm)/Formula 3: Formula 4 (95 wt %:5 wt %, 30 nm)/Formula 5 (20 nm)/LiF (1 nm)/Al (100 nm);

Light-emitting element 4#: ITO (100 nm)/NPD (60 nm)/Formula 2 (10 nm)/Formula 3: DPAVB (95 wt %:5 wt %, 30 nm)/Formula 5 (20 nm)/LiF (1 nm)/Al (100 nm);

Light-emitting element 5#: ITO (100 nm)/NPD (60 nm)/Formula 2 (10 nm)/Formula 3: Formula 4 (95 wt %:5 wt %, 30 nm)/Bphen (20 nm)/LiF (1 nm)/Al (100 nm);

Light-emitting element 6#: ITO (100 nm)/formula 1 (60 nm)/formula 2 (10 nm)/formula 3: formula 4 (95 wt %:5 wt %, 30 nm)/Bphen (20 nm)/LiF (1 nm)/Al (100 nm).

Light-emitting element 7#: ITO (100 nm)/Formula 1 (60 nm)/Formula 2 (10 nm)/Formula 3: DPAVB (95 wt %:5 wt %, 30 nm)/Bphen (20 nm)/LiF (1 nm)/Al (100 nm).

Light-emitting element 8#: ITO (100 nm)/Formula 1 (60 nm)/TCTA (10 nm)/Formula 3: DPAVB (95 wt %:5 wt %, 30 nm)/Formula 5 (20 nm)/LiF (1 nm)/Al (100 nm).

In order to compare the performance of the light-emitting elements according to the embodiments of the present disclosure, taking the bottom emission type structure which emits blue light as an example, the light-emitting elements of the comparative examples are designed as follows:

Comparative Element 1 is structured as follows:
ITO (100 nm)/NPD (60 nm)/Formula 2 (10 nm)/Formula 3: DPAVB (95 wt %:5 wt %, 30 nm)/Bphen (20 nm)/LiF (1 nm)/Al (100 nm);

Comparative Element 2 is structured as follows:
ITO (100 nm)/NPD (60 nm)/Formula 2 (10 nm)/DPEPO: DPAVB (95 wt %:5 wt %, 30 nm)/Bphen (20 nm)/LiF (1 nm)/Al (100 nm);

Comparative Element 3 is structured as follows:
ITO (100 nm)/NPD (60 nm)/TCTA 2 (10 nm)/DPEPO: DPAVB (95 wt %:5 wt %, 30 nm)/Bphen (20 nm)/LiF (1 nm)/Al (100 nm).

After these samples are prepared, the performance of the elements was measured using the Spectroscan PR 705 spectrometer and a Keithley 236 current-voltage source measurement system. The obtained measurement data is shown in Table 6 (V is the turn on voltage, EQE indicates the highest external quantum efficiency, and E/CIE-y indicates the ratio of the blue light efficiency to Y value of the color coordinate, for evaluating the blue light efficiency).

TABLE 6

| No. | voltage/V | EQE/% | E/CIE-y |
| --- | --- | --- | --- |
| Light-emitting element 1# | 3.75 | 5.25% | 42 |
| Light-emitting element 2# | 3.63 | 5.28% | 46 |
| Light-emitting element 3# | 3.64 | 5.29% | 46 |
| Light-emitting element 4# | 3.66 | 5.30% | 45 |
| Light-emitting element 5# | 3.70 | 5.32% | 44 |
| Light-emitting element 6# | 3.69 | 5.35% | 45 |
| Light-emitting element 7# | 3.68 | 5.34% | 44 |
| Light-emitting element 8# | 3.70 | 5.36% | 45 |
| Comparative Element 1 | 5.08 | 5.10% | 40 |
| Comparative Element 2 | 6.63 | 5.00% | 29 |
| Comparative Element 3 | 6.50 | 4.80% | 35 |

It can be known from the above experimental data, when the results of the turn on voltage, the external quantum efficiency and the blue light efficiency are taken as indexes for evaluation, the light-emitting elements (1#, 2#) with four layers containing the spirobifluorene compounds, the light-emitting elements (3#, 4#, 6#, 7#) with three layers containing the spirobifluorene compounds, and the light-emitting elements (5#, 8#) with two layers containing three spirobifluorene compounds can achieve a significant improvement of comprehensive effects, in particular, significant reduction of the turn on voltage, and significant improvement of the external quantum efficiency, compared with the Comparative Element 1 (only two layers contain the spirobifluorene compound, and two different spirobifluorene compounds in total) and the Comparative Element 2 (only one layer contains the spirobifluorene compound).

Although the present disclosure is described with respect to the preferred embodiments as above, these embodiments are not intended to limit the claims. The person skilled in the art is able to make several possible variations and modifications, without departing from the concept of the present disclosure. The protection scope of the present disclosure should be determined by the scope defined in the claims.

What is claimed is:

1. A light-emitting element, comprising
an anode,
a cathode placed opposite to the anode, and
a plurality of organic layers placed between the anode and the cathode,
wherein at least three of the plurality of organic layers each independently contains a compound having a spirobifluorene structure; or
wherein at least two of the plurality of organic layers each contains the compound having the spirobifluorene structure, and the at least two of the plurality of organic layers together contain at least three types of the compound having the spirobifluorene structure,
wherein the compound having the spirobifluorene structure, when contained in the plurality of organic layers, is selected from a group consisting of compounds represented by general formula I and combinations thereof:

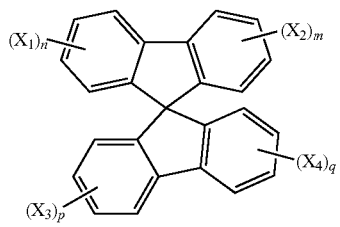

(I)

wherein each of $X_1$, $X_2$, $X_3$ and $X_4$ is independently selected from a group consisting of a hydrogen atom, an electron donating group, and an electron withdrawing group, and at least one of $X_1$, $X_2$, $X_3$ or $X_4$ is independently selected from a group consisting of the electron donating group and the electron withdrawing group; and
wherein n, m, p and q are integers each independently selected from a group consisting of 1, 2, 3 and 4,
wherein the electron withdrawing group is selected from a group consisting of a halogen atom, nitro, cyano, $C_1$-$C_{40}$ alkyl unsubstituted or substituted with a substituent, $C_6$-$C_{60}$ heteroarylamine unsubstituted or substituted with a substituent, $C_3$-$C_{60}$ heteroaryl unsubstituted or substituted with a substituent, $C_6$-$C_{60}$ aryl substituted with a substituent, and combinations thereof, wherein the substituent is selected from a group consisting of halogen atom, nitro, and cyano; and
wherein the electron donating group is selected from a group consisting of hydroxyl, $C_1$-$C_{40}$ alkoxyl unsubstituted or substituted with a substituent, $C_1$-$C_{40}$ alkyl unsubstituted or substituted with a substituent, $C_6$-$C_{60}$ aryl unsubstituted or substituted with a substituent, and combinations thereof, wherein the substituent is a hydroxyl group,
wherein the aryl group of the electron withdrawing group and the aryl group of the electron donating group are each independently selected from a group consisting of phenyl, naphthyl, phenanthryl, fluorenyl, and biphenyl; and
wherein the heteroaryl group is selected from a group consisting of furyl, thienyl, pyrrolyl, thiazolyl, imidazolyl, pyridyl, pyrazinyl, pyrimidinyl, pyridazinyl, indolyl, quinolinyl, carbazolyl, benzopyrroyl, benzopyridyl, dibenzofuranyl, dibenzothienyl, diphenyltriazinyl, and dipyridyl,
wherein the plurality of organic layers placed between the anode and the cathode comprises a hole transport layer, a light-emitting layer and an electron transport layer; and the plurality of organic layers placed between the anode and the cathode further comprises any one or more of a hole injection layer, an electron injection layer, an electron blocking layer, and a hole blocking layer,
wherein at least one of the hole injection layer, the hole transport layer and the electron blocking layer independently contains a compound having the spirobifluorene structure satisfying general formula I,
wherein the light-emitting layer contains a compound having the spirobifluorene structure satisfying general formula I, and
wherein at least one of the electron injection layer, the electron transport layer and the hole blocking layer independently contains a compound having the spirobifluorene structure satisfying general formula I.

2. The light-emitting element according to claim 1,
wherein in an instance in which the plurality of organic layers placed between the anode and the cathode further comprises the hole injection layer, the hole injection layer is placed between the anode and the hole transport layer; or
wherein in an instance in which the plurality of organic layers placed between the anode and the cathode further comprises the electron injection layer, the electron injection layer is placed between the cathode and the electron transport layer; or
wherein in an instance in which the plurality of organic layers placed between the anode and the cathode further comprises the electron blocking layer, the electron blocking layer is placed between the hole transport layer and the light-emitting layer; or
wherein in an instance in which the plurality of organic layers placed between the anode and the cathode further comprises the hole blocking layer, the hole blocking layer is placed between the electron transport layer and the light-emitting layer.

3. The light-emitting element according to claim 2,
wherein when both the electron transport layer and the hole blocking layer contain a compound having the spirobifluorene structure satisfying general formula I, the compound having a spirobifluorene contained in the electron transport layer and the compound having a spirobifluorene structure contained in the hole blocking layer are identical, and a compound having the spirobifluorene structure satisfying general formula I is present in at least one of the electron transport layer and the hole blocking layer in a doping form.

4. The light-emitting element according to claim 1,
wherein the at least three of the plurality of organic layers are adjacent to and overlap with one another; or
wherein the at least two of the plurality of organic layers are adjacent to and overlap with one another.

5. The light-emitting element according to claim 1, wherein a glass transition temperature Tg of the compounds having the spirobifluorene structure satisfying general formula I is greater than or equal to 120° C.

6. The light-emitting element according to claim 1,
wherein the electron withdrawing group is selected from a group consisting of groups represented by structural formulas as below:

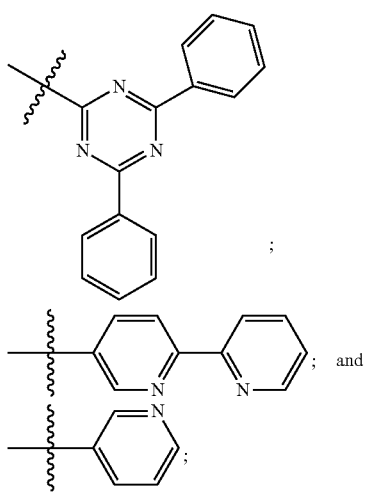

wherein the electron donating group is selected from a group consisting of groups represented by structural formulas as below:

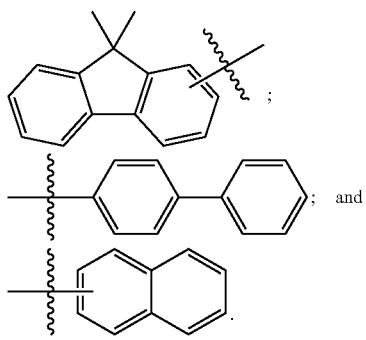

7. The light-emitting element according to claim 1, wherein the light-emitting layer comprises at least one host material and at least one doping material,
wherein the host material is selected from a group consisting of the compounds represented by general formula I, and at least one of the $X_1$, $X_2$, $X_3$, and $X_4$ is an electron withdrawing group.

8. The light-emitting element according to claim 1, wherein in the compound having the spirobifluorene structure satisfying general formula I of each of the at least one of the electron injection layer, the electron transport layer and the hole blocking layer, the $X_1$, $X_2$, $X_3$, and $X_4$ are independently selected from a group consisting of a hydrogen atom and an electron donating groups, and an electron mobility of the compound having the spirobifluorene structure satisfying general formula I is greater than a hole mobility of the compound having the spirobifluorene structure satisfying general formula I.

9. The light-emitting element according to claim 1, wherein in the compound having the spirobifluorene structure satisfying general formula I of each of the at least one of the hole injection layer, the hole transport layer and the electron blocking layer, each of the $X_1$, $X_2$, $X_3$, and $X_4$ is independently selected from a group consisting of a hydrogen atom and an electron withdrawing group, at least one of the $X_1$, $X_2$, $X_3$, and $X_4$ is an electron withdrawing group, and a hole mobility of the compound having the spirobifluorene structure satisfying general formula I is greater than an electron mobility of the compound having the spirobifluorene structure satisfying general formula I.

10. The light-emitting element according to claim 1, wherein the light-emitting layer comprises at least one host material and at least one doping material,
wherein the at least one doping material is selected from a group consisting of the compounds represented by general formula I, and the $X_1$, $X_2$, $X_3$, and $X_4$ are each independently selected from a group consisting of a hydrogen atom and an electron donating group.

11. A light-emitting element, comprising
an anode,
a cathode placed opposite to the anode, and
a plurality of organic layers placed between the anode and the cathode,
wherein at least three of the plurality of organic layers each independently contains a compound having a spirobifluorene structure; or
wherein at least two of the plurality of organic layers each contains the compound having the spirobifluorene structure, and the at least two of the plurality of organic layers together contain at least three types of the compound having the spirobifluorene structure,
wherein the compound having the spirobifluorene structure, when contained in the plurality of organic layers, is selected from a group consisting of compounds represented by general formula I and combinations thereof:

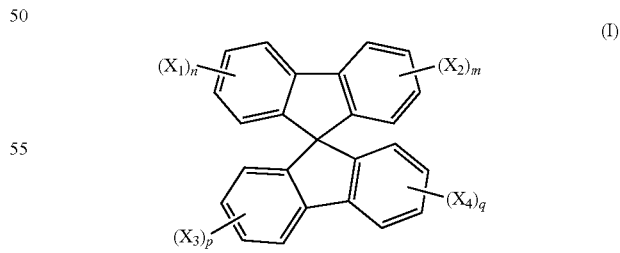

wherein each of $X_1$, $X_2$, $X_3$ and $X_4$ is independently selected from a group consisting of a hydrogen atom, an electron donating group, and an electron withdrawing group, and at least one of $X_1$, $X_2$, $X_3$ or $X_4$ is independently selected from a group consisting of the electron donating group and the electron withdrawing group; and wherein n, m, p and q are integers each independently selected from a group consisting of 1, 2, 3 and 4, wherein the electron withdrawing group is selected from a group consisting of a halogen atom, nitro, cyano, $C_1$-$C_{40}$ alkyl unsubstituted or substituted with a substituent, $C_6$-$C_{60}$ heteroarylamine unsubstituted or substituted with a substituent, $C_3$-$C_{60}$ heteroaryl unsubstituted or substituted with a substituent, $C_6$-$C_{60}$ aryl substituted with a substituent, and combinations thereof, wherein the substituent is selected from a group consisting of halogen atom, nitro, and cyano; and wherein the electron donating group is selected from a group consisting of hydroxyl, $C_1$-$C_{40}$ alkoxyl unsubstituted or substituted with a substituent, $C_1$-$C_{ao}$ alkyl unsubstituted or substituted with a substituent, $C_6$-$C_{60}$ aryl unsubstituted or substituted with a substituent, and combinations thereof, wherein the substituent is a hydroxyl group, wherein the aryl group of the electron withdrawing group and the aryl group of the electron donating group are each independently selected from a group consisting of phenyl, naphthyl, phenanthryl, fluorenyl, and biphenyl; and wherein the heteroaryl group is selected from a group consisting of furyl, thienyl, pyrrolyl, thiazolyl, imidazolyl, pyridyl, pyrazinyl, pyrimidinyl, pyridazinyl, indolyl, quinolinyl, carbazolyl, benzopyrroyl, benzopyridyl, dibenzofuranyl, dibenzothienyl, diphenyltriazinyl, and dipyridyl, wherein the plurality of organic layers placed between the anode and the cathode comprises a hole transport layer, a light-emitting layer and an electron transport layer;

and the plurality of organic layers placed between the anode and the cathode further comprises any one or more of a hole injection layer, an electron injection layer, an electron blocking layer, and a hole blocking layer, wherein at least one of the hole injection layer, the hole transport layer and the electron blocking layer independently contains a compound having the spirobifluorene structure satisfying general formula I; and wherein the light-emitting layer contains a compound having the spirobifluorene structure satisfying general formula I.

12. The light-emitting element according to claim 11, wherein the at least three of the plurality of organic layers are adjacent to and overlap with one another; or
wherein the at least two of the plurality of organic layers are adjacent to and overlap with one another.

13. The light-emitting element according to claim 11, wherein a glass transition temperature Tg of the compounds having the spirobifluorene structure satisfying general formula I is greater than or equal to 120° C.

14. A light-emitting element, comprising:
an anode,
a cathode placed opposite to the anode, and
a plurality of organic layers placed between the anode and the cathode,
wherein at least three of the plurality of organic layers each independently contain a compound having a spirobifluorene structure; or
wherein at least two of the plurality of organic layers each contain the compound having the spirobifluorene structure, and the at least two organic layers together contain at least three types of the compound having the spirobifluorene structure, wherein the compound having the spirobifluorene structure, when contained in the plurality of organic layers, is selected from a group consisting of compounds represented by general formula II, and combinations thereof:

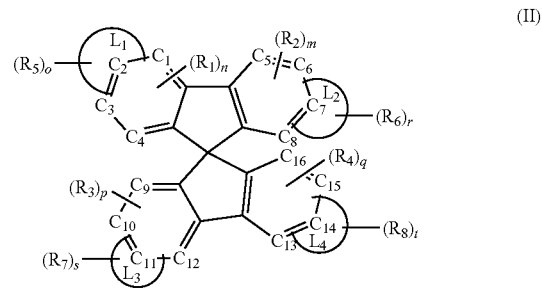

(II)

wherein at least one of ring structure $L_1$, ring structure $L_2$, ring structure $L_3$, and ring structure $L_4$ is present in general formula II and is independently an aromatic ring having 6-42 carbon atoms;

wherein when the ring structure $L_1$ is present in general formula II, the ring structure $L_1$ is fused to $C_1$ and $C_2$, $C_2$ and $C_3$, or $C_3$ and $C_4$;

wherein when the ring structure $L_2$ is present in general formula II, the ring structure $L_2$ is fused to $C_5$ and $C_6$, $C_6$ and $C_7$, or $C_7$ and $C_8$;

wherein when the ring structure $L_3$ is present in general formula II, the ring structure $L_3$ is fused to $C_9$ and $C_{10}$, $C_{10}$ and $C_{11}$, or $C_{11}$ and $C_{11}$;

wherein when the ring structure $L_4$ is present in general formula II, the ring structure $L_4$ is fused to $C_{13}$ and $C_{14}$, $C_{14}$ and $C_{15}$, or $C_{15}$ and $C_{16}$;

wherein $R_1$, $R_2$, $R_3$, $R_4$, $R_5$, $R_6$, $R_7$, and $R_8$ are independently selected from a group consisting of a hydrogen atom, an electron donating group and an electron withdrawing group; and wherein n, m, p, q, o, r, s, and t are integers each independently selected from a group consisting of 1, 2, 3 and 4.

15. The light-emitting element according to claim 14, wherein the plurality of organic layers placed between the anode and the cathode comprises a light-emitting layer, the light-emitting layer contains at least one host material and at least one doping material, and the host material and the doping material are independently selected from a group consisting of compounds represented by general formula II; and
when the doping material is selected from a group consisting of the compounds represented by general formula II, each of $R_1$, $R_2$, $R_3$, $R_4$, $R_5$, $R_6$, $R_7$, and $R_8$ are independently selected from a hydrogen atom and an electron donating group.

16. A light-emitting element, comprising:
an anode,
a cathode placed opposite to the anode, and
a plurality of organic layers placed between the anode and the cathode,
wherein at least three of the plurality of organic layers each independently contains a compound having a spirobifluorene structure; or
wherein at least two of the plurality of organic layers each contain the compound having the spirobifluorene structure, and the at least two of the plurality of organic layers together contain at least three types of the compound having the spirobifluorene structure, wherein the plurality of organic layers placed between the anode and the cathode comprises a hole transport layer, a light-emitting layer and an electron transport layer;

wherein the plurality of organic layers placed between the anode and the cathode further comprises a hole injection layer, and a hole blocking layer, wherein both the hole injection layer and the electron blocking layer contain a compound having a spirobifluorene structure, the compound having a spirobifluorene structure contained in the hole injection layer and the compound having a spirobifluorene structure contained in the electron blocking layer are identical, and a compound having a spirobifluorene structure is present in at least one of the hole injection layer and the electron blocking layer in a doping form.

17. A display device, comprising a light-emitting element, wherein the light-emitting element comprises:

an anode, a cathode placed opposite to the anode, and a plurality of organic layers placed between the anode and the cathode, wherein at least three of the plurality of organic layers each independently contain a compound having a spirobifluorene structure; or wherein at least two of the plurality of organic layers each contain the compound having the spirobifluorene structure, and the at least two organic layers together contain at least three types of the compound having the spirobifluorene structure, wherein the compound having the spirobifluorene structure, when contained in the organic layers, is selected from a group consisting of compounds represented by general formula I and combinations thereof:

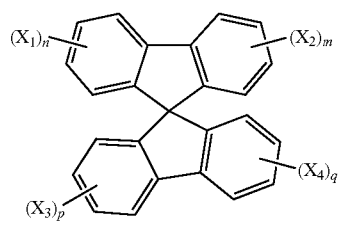

(I)

wherein $X_1$, $X_2$, $X_3$ and $X_4$ are each independently selected from a group consisting of a hydrogen atom, an electron donating group and an electron withdrawing group, and at least one of $X_1$, $X_2$, $X_3$ and $X_4$ are each independently selected from a group consisting of the electron donating group and the electron withdrawing group; and wherein n, m, p and q are integers each independently selected from a group consisting of 1, 2, 3 and 4, wherein the electron withdrawing group is selected from a group consisting of a halogen atom, nitro, cyano, $C_1$-$C_{40}$ alkyl unsubstituted or substituted with a substituent, $C_6$-$C_{60}$ heteroarylamine unsubstituted or substituted with a substituent, $C_3$-$C_{60}$ heteroaryl unsubstituted or substituted with a substituent, $C_6$-$C_{60}$ aryl substituted with a substituent, and combinations thereof, wherein the substituent is selected from a group consisting of halogen atom, nitro, and cyano; and wherein the electron donating group is selected from a group consisting of hydroxyl, $C_1$-$C_{40}$ alkoxyl unsubstituted or substituted with a substituent, $C_1$-$C_{40}$ alkyl unsubstituted or substituted with a substituent, $C_6$-$C_{60}$ aryl unsubstituted or substituted with a substituent, and combinations thereof, wherein the substituent is a hydroxyl group, wherein the aryl group of the electron withdrawing group and the aryl group of the electron donating group are each independently selected from a group consisting of phenyl, naphthyl, phenanthryl, fluorenyl, and biphenyl;

wherein the heteroaryl group is selected from a group consisting of furyl, thienyl, pyrrolyl, thiazolyl, imidazolyl, pyridyl, pyrazinyl, pyrimidinyl, pyridazinyl, indolyl, quinolinyl, carbazolyl, benzopyrroyl, benzopyridyl, dibenzofuranyl, dibenzothienyl, diphenyltriazinyl, and dipyridyl, wherein the plurality of organic layers placed between the anode and the cathode comprises a hole transport layer, a light-emitting layer and an electron transport layer;

and the plurality of organic layers placed between the anode and the cathode further comprises any one or more of a hole injection layer, an electron injection layer, an electron blocking layer, and a hole blocking layer, wherein at least one of the hole injection layer, the hole transport layer and the electron blocking layer independently contains a compound having the spirobifluorene structure satisfying general formula I, wherein the light-emitting layer contains a compound having the spirobifluorene structure satisfying general formula I, and wherein at least one of the electron injection layer, the electron transport layer and the hole blocking layer independently contains a compound having a spirobifluorene structure satisfying general formula I.

* * * * *